United States Patent [19]

Moor

[11] 4,120,304
[45] Oct. 17, 1978

[54] NASO-GASTRIC TUBE HOLDER

[76] Inventor: Burdette J. Moor, 2029 S. 146 Cir., Omaha, Nebr. 68144

[21] Appl. No.: 731,185

[22] Filed: Oct. 12, 1976

[51] Int. Cl.² .......................................... A61M 25/00
[52] U.S. Cl. ............................ 128/348; 128/DIG. 26
[58] Field of Search ................. 128/348, 349 R, 350, 128/351, 133, DIG. 26, 214 R

[56] References Cited

U.S. PATENT DOCUMENTS

| 3,046,989 | 7/1962 | Hill | 128/348 |
|---|---|---|---|
| 3,146,778 | 9/1964 | Krawiec | 128/348 X |
| 3,677,250 | 7/1972 | Thomas | 128/348 |
| 3,977,407 | 8/1976 | Coleman et al. | 128/348 |

Primary Examiner—John D. Yasko
Attorney, Agent, or Firm—Henderson, Strom, Sturm, Cepican & Fix

[57] ABSTRACT

An apparatus for holding a naso-gastric tube in position relative to a patient's nares, while at the same time permitting a reasonable degree of freedom for the patient to move without significant discomfort. The device includes a clamp for fixedly and movably engaging a naso-gastric tube and an adhesive member for affixing the device to a patient's nose. These two elements are connected by a flexible elongate member which allows relative movement therebetween. The tube clamp frictionally engages the exterior of the tube and thus allows the tube to be manually moved relative thereto for repositioning.

6 Claims, 6 Drawing Figures

NASO-GASTRIC TUBE HOLDER

BACKGROUND OF THE DISCLOSURE

This invention relates generally to tube holding devices, and specifically to an improved device for holding a naso-gastric tube in position relative to a patient's nares.

It has long been the practice in the medical field to affix naso-gastric tubes within a patient's nares by securing the tube to the patient's nose with several strips of adhesive tape or the like. There is no specific way, or manner, which has become accepted practice for affixing the tape on the nose; however, the general result is usually an unsightly, inconvenient and uncomfortable conglomeration of tape elements running around the nose and tube. Because it is medically necessary to periodically reposition the tube within the patient's body, this conglomeration of tape must be removed. Obviously, after removal, the initial positioning procedure must be repeated; and it should be noted that the tape is not reusable. Usually, when the tube is reapplied, the new tape is placed in position in the same general location as the original tape and eventually the skin becomes tender to the point where it is extremely painful to the patient.

BRIEF SUMMARY OF THE INVENTION

It is an object of this invention to provide a device for holding a naso-gastric tube in position relative to a patient's nares.

Another object of this invention is to provide a device for holding a naso-gastric tube in position relative to a patient's nares which allows the tube to be longitudinally moved relative to the nares without the necessity of removing the device from the patient's nose.

Another object of this invention is to provide a device for holding a naso-gastric tube in position which is relatively simple, inexpensive, yet durable.

Another object of this invention is to provide a naso-gastric tube holding device which is easily cleaned and inhibits the accumulation of pathogens, bacteria and similar potential sources of infection.

Another object of this invention is to provide a naso-gastric tube holding device which employs an adhesive member to affix the device to a patient's nose.

Yet another object of this invention is to provide a naso-gastric tube holding device which does not interfere with the patient's peripheral field of vision.

It is the further object of this invention to provide a naso-gastric tube holding device which is easily applied by a single person without the need for special tools or equipment.

It is a still further object of this invention to provide a naso-gastric tube holding device which allows relative movement of the tube, and thus eliminates the danger of pressure necrosis of the nasal septum of ali nasi.

The foregoing objects and others are accomplished in accordance with the invention by providing an apparatus for holding a naso-gastric tube in position relative to a patient's nares, while at the same time permiting a reasonable degree of freedom for the patient to move without significant discomfort. The device includes a clamp for fixedly and movably engaging a naso-gastric tube and an adhesive member for affixing the device to a patient's nose. These two elements are connected by a flexible elongate member which allows relative movement therebetween. The tube clamp frictionally engages the exterior of the tube and thus allows the tube to be manually moved relative thereto for repositioning.

BRIEF DESCRIPTION OF THE DRAWINGS

For a better understanding of the invention as well as other objects and further features thereof, reference is made to the following detailed disclosure of the invention taken in conjunction with the accompanying drawings wherein.

DESCRIPTION OF THE PREFERRED EMBODIMENTS

Figure 1:
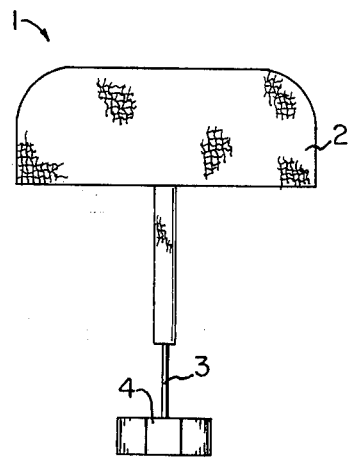
FIG. 1 is a top plan view of one embodiment of the tube holding device.

Referring now to FIG. 1, an embodiment of the naso-gastric tube holding device of the invention is generally designated at 1. The device includes three primary elements, i.e., an adhesive member, a clamp and a flexible coupler therebetween. Adhesive member 2 comprises a flexible material such as thin plastic or cloth having one side covered with a layer of adhesive. The member 2 is shown to have a generally inverted U-shaped planar configuration to better fit across the forward portion of the patient's nose without extending up the bridge of the nose and into the peripheral field of vision.

Figure 2:
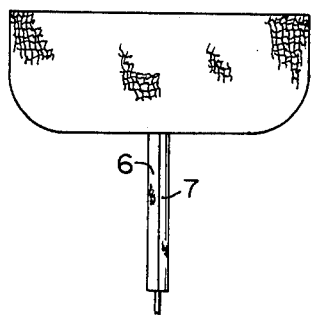
FIG. 2 is a partial top plan view of a modified embodiment thereof.

An elongate flexible coupling member 3 is connected on one end to the adhesive member and extends away therefrom for connection on the other end to clamp 4. Connection may be made between the adhesive member and the coupling member in any suitable manner, such as, for example, by folding preformed flaps 6 and 7 on member 2 around the coupling and securing them with adhesive (see FIG. 2). Also, the connection between the coupling and the clamp may be done in any suitable manner such as by drilling a hole in the clamp and inserting the coupling for adhesive securement. Coupling 3 may be of any suitable material such as plastic and may have any cross-sectional shape such as round, square, etc.

Figure 3:
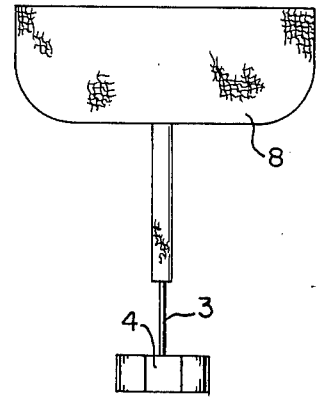
FIG. 3 is a top plan view of the modified embodiment the tube holding device of the instant invention.

FIG. 3 shows a modification of the adhesive member having a different planar configuration. In this figure, the adhesive member 8 is U-shaped. This configuration, like that of FIG. 1, advantageously fits over the forward portion of the nose out of the peripheral field of vision of the patient.

Figure 4:
FIG. 4 is a partial side elevational view of the adhesive member used to hold the device of the instant invention to the patient's nose.

Referring now to FIG. 4, the partial side elevational layer structure of the adhesive member can be seen. A layer of adhesive 9 is placed on the flexible layer 2 and becomes substantially an integral part thereof. A removable, flexible sheet 10 is in contact with the adhesive layer 9 to protect same until the device is to be used. Sheet 10 has been treated with an adhesive releasing agent so that it may be easily stripped from the layer 9 without damage to the adhesive layer. Adhesive members with this type of structure are well-known in the art, and further description here would serve no useful purpose.

Figure 5:
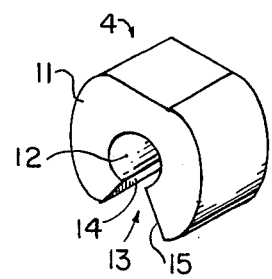
FIG. 5 is a perspective view of the clip of the instant invention which affixes to the naso-gastric tube.

The clamp shown in FIG. 5 is of one-piece construction and comprises a rigid generally circular disc 11 having a hole 12 and slot 13 cut therethrough. Of course, it is not important what the shape of the member 11 is, only that it has a slot and hole therethrough. The hole 12 is substantially the same size as the exterior dimension of the tube to be held. The slot 13 should be of sufficient size to allow the tube to snap into the hole for secure holding. The slot is shown to have sloping sides 14 and 15 which aid in alignment and connection.

Figure 6:
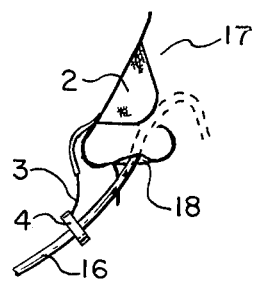
FIG. 6 is a partially perspective side elevational view of the tube holding device of the instant invention showing it in position on a patient's nose holding the naso-gastric tube in proper location.

FIG. 6 shows the device on a patient's nose 17 holding the naso-gastric tube 16 in proper position relative to the nares 18. In this position, the tube 16 is free to move relative to the patient's nares, but not to move longitudinally away therefrom. The patient thus has a convenient degree of freedom with minimum discomfort. Also, it can be readily seen that the tube 16 may easily be manually moved in either longitudinal direction merely by holding the clamp 4 while either pushing or pulling the tube. There are no critical dimensions for the elements of the device, but it has been found that coupling 3 is advantageously less than two inches long, though larger or smaller dimensions may prove suitable under certain circumstances.

It will be understood that various changes in the details, materials, steps and arrangements of parts, which have herein been described and illustrated in order to explain the nature of the invention, will occur to and may be made by those skilled in the art upon a reading of the disclosure within the principles and scope of the invention.

For example, it has been found advantageous to color member 2 approximately the same as the patient's skin. This, obviously, interferes less with vision and thus increases the user's comfort.

Also, the inner surface of hole 12 in clamp 4 may advantageously be scored or otherwise modified to improve its gripping characteristics.

I claim:

1. Apparatus for holding a naso-gastric tube in position relative to a patient's nares comprising
    (a) a rigid slotted holding means removably attached and adapted to be selectively movably affixed by frictional engagement to the naso-gastric tube
    (b) adhesive securing means adapted to be removably affixed to the exterior of the patient's nose; and
    (c) flexible elongate connector means affixed at one end to said holding means, and affixed at the other end to said adhesive securing means.

2. The apparatus of claim 1 wherein said adhesive securing means comprises a substantially flexible sheet member having a layer of adhesive on one surface thereof.

3. The appartus of claim 2 wherein sid adhesive securing means further comprises a flexible removable protective sheet covering, and in contact with, said layer of adhesive, said protective sheet including an adhesive releasing material thereon.

4. The apparatus of claim 3 wherein said sheet member and protective sheet have a substantially broadened U-shaped planar configuration.

5. The apparatus of claim 4 wherein said holding means comprises a C-shaped clamp adapted to frictionally engage the exterior of the naso-gastric tube.

6. The apparatus of claim 3 wherein said sheet member and protective sheet have a substantially broadened inverted U-shaped planar configuration.

* * * * *